US009129588B2

(12) United States Patent
Lyons

(10) Patent No.: US 9,129,588 B2
(45) Date of Patent: Sep. 8, 2015

(54) CONFIGURABLE NOISE CANCELLING SYSTEM

(75) Inventor: Matthew Lyons, York, PA (US)

(73) Assignee: Definitive Technology, LLC, Owings Mills, MD (US)

( * ) Notice: Subject to any disclaimer, the term of this patent is extended or adjusted under 35 U.S.C. 154(b) by 354 days.

(21) Appl. No.: 13/620,807

(22) Filed: Sep. 15, 2012

(65) Prior Publication Data

US 2014/0079235 A1 Mar. 20, 2014

(51) Int. Cl.

| | |
|---|---|
| ***A61F 11/06*** | (2006.01) |
| ***G10K 11/16*** | (2006.01) |
| ***H03B 29/00*** | (2006.01) |
| ***G10K 11/178*** | (2006.01) |
| ***H04R 1/10*** | (2006.01) |

(52) U.S. Cl.

CPC ............ *G10K 11/178* (2013.01); *H04R 1/1083* (2013.01); *G10K 2210/1081* (2013.01); *G10K 2210/3014* (2013.01); *G10K 2210/3045* (2013.01); *G10K 2210/3056* (2013.01)

(58) Field of Classification Search

None

See application file for complete search history.

(56) References Cited

U.S. PATENT DOCUMENTS

| | | | | |
|---|---|---|---|---|
| 2008/0025523 | A1 | 1/2008 | Miller | |
| 2010/0105447 | A1 * | 4/2010 | Sibbald et al. | 455/570 |
| 2013/0039506 | A1 * | 2/2013 | Oide | 381/71.6 |

OTHER PUBLICATIONS

Horvath, T., "Equalizer—Advanced Music player and eq", CNET Download.com, http://download.cnet.com/Equalizer-Advanced-Music-player-and-eq/3000-2133_4-75022812.html, screen capture Jan. 4, 2013.

"iPhone 4 iPod noise cancelling feature", MacTalk, http://www.mactalk.com.au/31/90553-iphone-4-ipod-noise-cancelling-feature.html, screen capture Nov. 20, 2011.

"Noise Cancelling Program on iPhone", modmyi.com, Noise Cancelling Program on iPhone, screen capture Nov. 20, 2011.

Tucker, L., "Share Your Music Easily With MyStream App [iPhone]", TechEasier, http://maketecheasier.com/share-your-music-easily-with-mystream-app-iphone/2011/08/29, screen capture Nov. 20, 2011.

* cited by examiner

*Primary Examiner* — Regina N Holder

(74) *Attorney, Agent, or Firm* — Fish & Tsang LLP

(57) ABSTRACT

Systems, devices, and methods for customizable reduction of perceived ambient sounds are disclosed. Customizable reduction can be achieved via an application operable in conjunction with an audio player or a headset having a microphone.

15 Claims, 4 Drawing Sheets

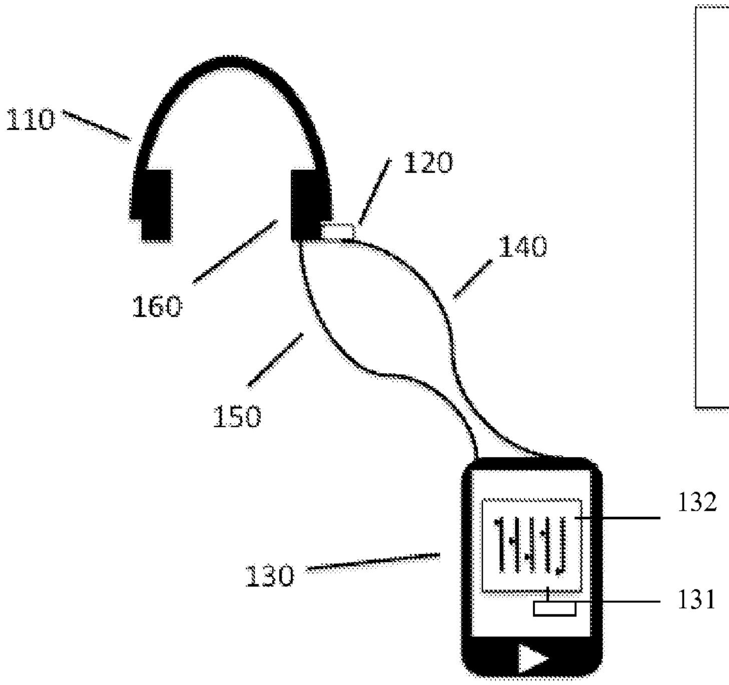
Figure 1A
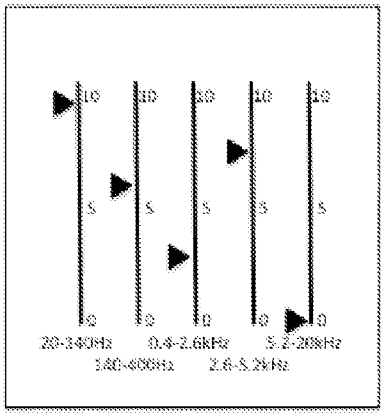
Figure 1B
Figure 1

CONFIGURABLE NOISE CANCELLING SYSTEM

FIELD OF THE INVENTION

The field of the invention is noise cancelling systems for use with audio players and similar devices.

BACKGROUND

The following background discussion includes information that may be useful in understanding the present inventive subject matter. It is not an admission that any of the information provided herein is prior art or relevant to the presently claimed inventive subject matter, or that any publication specifically or implicitly referenced is prior art.

Excessive and distracting background noise is a well known issue in many environments, interfering with effective communication, the ability to focus and concentrate, and the enjoyment of recreational activities such as music and film. Historically, efforts at reducing the impact of background noise have focused on occlusion of the ear canal by such means as tightly fitted ear plugs or insulated cups that fit tightly about the outer ear. Commercial headsets, such as those intended for use with mobile telephones or for personal audio players, commonly employ earbuds that cover or are partially inserted into the ear canal. While this positions them advantageously for at least partially blocking background sounds, particularly noisy environments may leave the user with little recourse other than increasing the volume.

More recently some manufacturers, notably Bose™ and Sennheiser™, have introduced specialized headphones or headsets that incorporate active noise cancellation features. In such devices a microphone incorporated into the headset receives background sounds from the environment. This sound is translated into a waveform, which is then processed to generate a sound cancellation waveform that is 180 degrees out of phase with the sound received by the microphone. This sound cancellation waveform is transmitted to speakers incorporated into the headset, where it is expected to reduce the background sounds perceived by the user. The sound cancellation waveform may also be combined with a desired sound signal, such as music, that is transmitted to the speakers simultaneously. Some of these devices, notably the Bose QC1 and QC2, have a feature that allows the user to select between low and high levels of sound cancellation.

The increasing processing power of personal devices such as personal audio players and mobile telephones, has led to the development of software applications for such devices that can generate noise cancelling signals. Such software applications permit the addition of noise cancelling features to a system that incorporates relatively inexpensive general purpose headsets. US patent publication no. 2008/0025523 describes a software application that utilizes a background sound signal obtained from a microphone that is part of a headset to generate a noise cancellation waveform that is 180 degrees out of phase with the background sound within a portable communication device. This noise cancellation waveform is then added to the audio feed supplied to the headset. The application also allows the user to exclude specific sound frequency ranges from noise cancellation.

Such active noise cancellation systems have some degree of effectiveness at reducing unwanted background noise while preserving sounds the user wishes to perceive, however there are drawbacks. Addition of the noise cancelling waveform to the audio feed of a speaker can result in partial cancellation of a desired audio signal, such as music or speech, resulting in undesirable distortion of the perceived sound. Adjustment of the degree of noise cancellation by, for example, the selection of a “low” or “high” setting, only allows a user to reduce this effect in a nonselective manner, and has limited utility at high background noise levels. Exclusion of specific sound frequency ranges from noise cancellation can exacerbate this distortion, in addition to rendering such noise cancellation systems less effective if the nature of the undesired background noise changes.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Thus, there is still a need for a system that can provide effective noise cancellation across a range of environmental conditions while minimizing the loss of perception of desired sounds by the user.

SUMMARY OF THE INVENTION

The inventive subject matter provides apparatus, systems and methods in which a noise reduction application is configured to allow a user to control the level of noise reduction that is applied to different frequency ranges. The system could also include a headset and an audio player capable of both playing audio files and implementing a noise reduction application or program.

A user could configure an active noise canceling system to utilize a variety of noise reduction profiles, such profiles providing a set of relative degrees of noise cancellation that is applied to a set of frequency ranges. This allows a user to select a noise canceling mode that is at least partially optimized for a listening environment or desired audio feed.

It is contemplated that a noise reduction software application could control a microprocessor in a headset or an audio player to automate noise canceling.

As used herein, the term “audio players” includes any device or software (e.g., software stored in a device) configured to play an audio stream, including for example, a tablet computer, a media player, a mobile phone, a computing device, a cassette player, a compact disc player, a DVD player, a computer software configured to play media files, an iPhone™, or an iPod™.

In one aspect of the inventive subject matter, the system comprises a headset that includes a speaker and a microphone, an audio player with the capability of implementing a noise cancelling application, and a noise cancelling application. The noise cancelling application could provide a user interface, by which the user could assign relative levels of noise cancellation to different frequency ranges that are received by the microphone of the headset. The relative levels of noise cancellation could be achieved at least in part by altering amplitudes or phases of signals being sent to a speaker. In some embodiments the user may select or control relative levels of noise cancellation by selecting a profile from among a set of profiles, such as for example, a set of environmental profiles. Such environmental profiles include, but are not limited to, an office-related profile, a transportation-related profile (e.g., airplane mode, train mode, etc.), and a home-related profile. The frequency ranges associated with such profiles may be continuous or discontinuous.

In some embodiments the user interface could be a graphical user interface. A graphical user interface of the application could provide virtual designators that are associated with frequency ranges; in such an embodiment, manipulation or movement of a designator can be used to control the level of noise cancellation assigned to an associated frequency range. In other embodiments the user interface allows the concurrent application of different profiles.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 is a representation of a configurable noise cancellation system of the inventive subject matter. FIG. 1A shows a headset with an associated microphone in combination with an audio player, which is showing a graphic user interface that may be used for generating and utilizing a noise cancellation profile. FIG. 1B is a graphic representation of a such a graphic user interface, showing movable designators that are associated with different frequency ranges and that permit a user to assign a relative degree of noise cancellation to such an associated frequency range.

DETAILED DESCRIPTION

Figure 2:
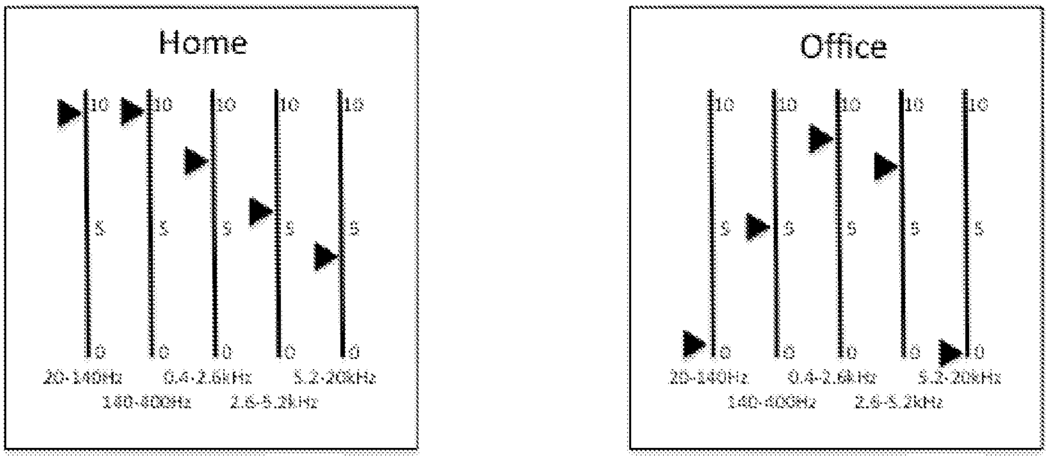
FIG. 2 is a graphic representation of a user interface displaying different environment-related noise cancellation profiles.

It should be noted that while the following description is drawn to a noise cancelling system that utilizes a portable audio device, such as a mobile telephone or a portable audio player, various alternative configurations are also deemed suitable and may employ audio devices including personal radios and other personal communication devices, assistive devices for the hearing impaired, and communication systems such as those found in vehicles and other high noise environments. One should appreciate that such devices may include computing devices that comprise a processor configured to execute applications or software instructions stored on a tangible, non-transitory computer readable storage medium (e.g., hard drive, solid state drive, RAM, flash, ROM, etc.). The application or software instructions preferably configure the computing device to provide the roles, responsibilities, or other functionality as discussed below with respect to the disclosed system. The techniques disclosed and claimed herein are equally applicable to hard-wired configurations in which a cable or cord provides a connection or connections between a headset and a portable audio device and to wireless configurations in which a radio signal provides such a connection or connections.

One should appreciate that the disclosed techniques provide many advantageous technical effects including reduction of the distortion of desired audio signals when noise cancellation is applied, improved ability to perceive desired environmental sounds, and effective noise cancellation across different environments and settings.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In one embodiment of the inventive subject matter, a noise cancelling system includes a headset or headphones and an audio player. The headset or headphones include a speaker for transduction of an audio signal to audible sound and a microphone. The audio player, in addition to having the capacity to play an audio file, is also able to implement a noise cancelling application or set of software instructions. Such an application includes a user interface that permits a user to control the relative level of noise cancellation that is applied to different frequencies or frequency ranges that are received from the environment by the microphone. Such frequency ranges may be discontinuous. Control of the level or degree of noise cancellation can, for example, be implemented by adjusting the amplitude of a noise cancelling signal as generated by the application. In some embodiments the user interface allows the user to select noise cancellation profiles that associate a set of relative levels of noise cancellation with a set of sound frequencies or frequency ranges. The user interface may permit a user to generate a noise cancellation profile, select a noise cancellation profile provided with the system, or both generate and select pre-provided noise cancellation profiles. In some embodiments the system can perform a sampling operation in which input from the microphone is used to characterize the background noise. In such an embodiment a frequency profile of the background noise may be displayed and/or stored, for use by the user or the application in generating a noise cancellation profile appropriate for the sampled environment.

In some embodiments of the inventive subject matter, the noise cancellation signal is combined with a signal from a stored audio file and transmitted to a speaker in order to provide the contents of the audio file to the user with a reduced perception of background noise. In other embodiments, the noise cancellation signal is combined with an audio signal received from a secondary source, such as a mobile telephone device or an assistive hearing device, and transmitted to a speaker in order to provide the contents of the audio signal to a user with a reduced perception of background noise. In still another embodiment the noise cancellation signal is provided to a speaker without combination, in order to reduce the perception of background noise by a user and provide relative silence. In yet another embodiment, the system may support two or more of the combination of the noise cancellation signal with a stored audio file, combination of the noise cancellation signal with an audio signal from a secondary source, and provision of the noise cancellation signal without combination.

In some embodiments of the inventive subject matter noise cancellation profiles may be categorized into types. Different profile types, including, but not limited to, environmental profiles, audio file profiles, and environmental cue profiles may be selectable by the user through the user interface. It is also contemplated that a user could create their own profiles or profile types, or combine or modify existing profiles or profile types, to better suit particular environments or audio files. Environmental profiles could be configured to maximize effective noise cancellation based on the acoustic profile of the noisy environment. Environmental profiles can include an office-related profile and a home-related profile, and may, for example, be configured to provide higher levels of noise reduction at frequency ranges associated with background noises in these environments while reducing the negative impact of noise cancellation at frequencies where it is not needed. Audio file profiles may be configured to minimize perceived distortion of a combined signal and maximize effective noise cancellation based on the acoustic profile of the audio file, for example providing lower levels of noise reduction in frequency ranges where the volume of generated by the audio file is typically relatively high and provides an inherent degree of masking of background noise. Environmental cue profiles may be configured to provide reduced levels of noise reduction in frequency ranges where the user may wish to perceive environmental sounds (ex: keystrokes, a doorbell, an automobile horn) thereby allowing a user to perceive important environmental cues while reducing distracting background noise. In some embodiments the user interface may permit a user to apply multiple noise cancellation profiles concurrently. The use of noise cancellation profiles and the ability to switch freely between them advantageously permits a system of the inventive concept to provide effective noise cancellation as the user moves between different environments and/or moves between different tasks In some preferred embodiments of the inventive subject matter, the user interface is a graphic user interface. Such an interface can include one or more virtual designators that are associated with certain frequency ranges. In such an embodiment, movement of these virtual designators may be used to control the relative level of noise cancellation applied to the associated frequency range. In some other preferred embodiments, the user interface could allow the user to directly input a value into a field associated with a frequency range, the value indicating the relative degree of noise cancellation to be applied to the frequency range. In such an embodiment frequency ranges may be displayed in a tabular format with associated fields for value entry, or any other suitable format. In some embodiments the application could allow the user to create, switch between or select different user interfaces.

In FIG. 1A an embodiment of a system of the inventive subject matter is shown that includes a stereo headphone 110 with an associated microphone 120 and a personal audio device 130. Environmental sounds are received by the microphone 120 and translated into a background noise signal that is transmitted to a personal audio device 130 using an input cord 140. As noted above, in some embodiments transmission of the background noise signal can be accomplished by wireless transmission. The personal audio device 130 is shown displaying a graphic user interface 132 of an application 131 that is configured to process the incoming background noise signal to produce a noise cancellation signal that is returned to the speaker of the headphone 160 using an audio output cord 150. As noted above, in some embodiments, transmission of the noise cancellation signal could be accomplished by wireless transmission. FIG. 1B shows an enlarged view of the graphics user interface shown on the personal audio device in FIG. 1A. In this example, a triangular designator is associated with each member of a set of frequency ranges, and could be moved from a relative value of a range (e.g., 0-10, 0-100, 0-1,000, 500-10,000, etc.) to indicate a level of noise cancellation that is to be applied to the associated frequency range.

FIG. 2 shows a graphic user interface of the inventive concept displaying different noise cancellation profiles associated with different operating environments. The "Home" environment profile indicates high levels of noise cancellation applied at lower frequency ranges to address the prevalence of low frequency background noise in such an environment. Such background noise may be generated by, for example, traffic on nearby roadways and lawn equipment. Relatively lower levels of noise cancellation are applied at higher frequencies where background noise is less prevalent, providing some noise cancellation while reducing the distortion of perceived sounds from (for example, from a stored audio file) in these frequency ranges. The "Office" environmental profile indicates high levels of noise cancellation applied at midrange frequencies, thereby maximizing the perceived reduction in background sounds from components of such an environment, such as printers, photocopiers, and similar devices while minimizing distortion while still providing a desired degree of noise cancellation in low and high frequency range.

Figure 3:
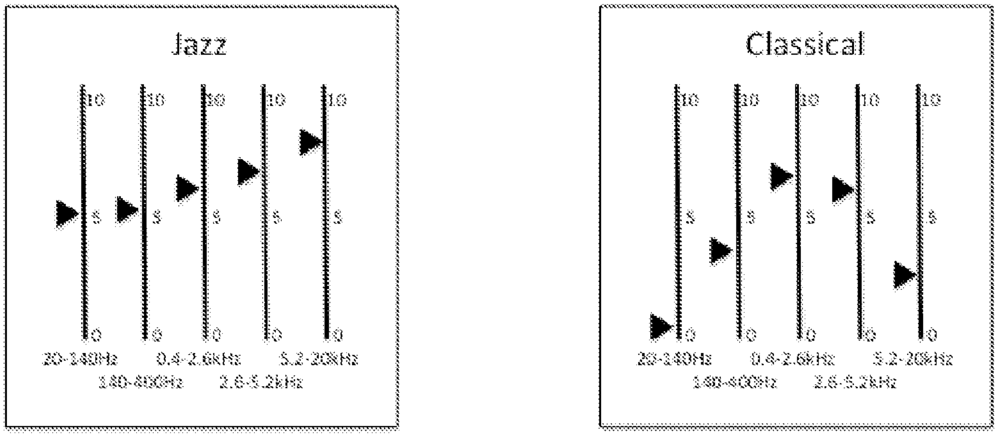
FIG. 3 is a graphic representation of a user interface displaying noise cancellation profiles associated with different music genres.

FIG. 3 shows a graphic user interface of the inventive concept displaying different profiles associated with different audio files, which could be utilized when the noise cancellation signal is combined with audio files. In such applications, both background noise and the distortion audible in the combined signal may be objectionable to some users. As shown, a "Jazz" music genre profile could have moderate levels of noise cancellation at low and mid frequency ranges, where generally greater volume tends to obscure background noise with reduced distortion due to the combined signal, and higher levels of noise cancellation at higher frequencies where volume could be reduced. Similarly, a "Classical" music genre profile could provide reduced noise cancellation at low and high frequencies, where generally higher volume in these ranges could serve to obscure background noise with reduced distortion from the combined signal.

Figure 4:
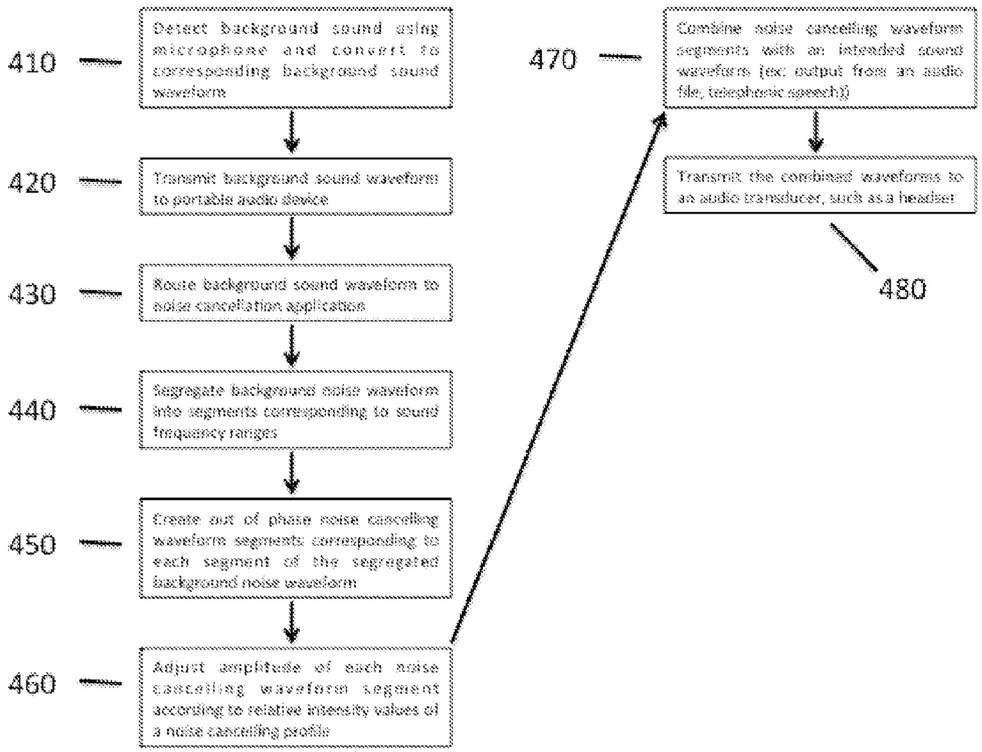
FIG. 4 is a flowchart describing a software implemented configurable noise cancelling process in a portable audio device.

A flowchart that illustrates the operation of an embodiment of a noise cancellation application of the inventive subject matter is shown in FIG. 4. In the initial step 410 background sounds (or noise) are detected by the microphone, which converts the sounds to an electrical signal in the form of a background sound waveform. In the next step 420 the background sound waveform is transmitted to a portable audio device, where it is routed to a noise cancellation application in 430. The background sound waveform is then segregated into segments that correspond to frequency ranges 440. The application creates a set of cancelling waveform segments that correspond to the background sound waveform segments but are 180 degrees out of phase 450. The level of noise cancellation is then adjusted for each of the noise cancellation waveform segments based on the noise cancellation profile, by, for example, adjusting the amplitude of the waveform 460. The adjusted noise cancellation waveform segments are then combined with an intended sound waveform, for example from a stored audio file or cellular telephone circuit 470, and the combined waveforms subsequently transmitted to a speaker or other audio transducer 480.

A noise reduction application could comprise instruction sets operable on audio players or headsets (e.g., a microprocessor composing an audio player or a headset). Instruction sets could be configured to cause a device (e.g., an audio player, a headset, etc.) to receive a signal indicative of sounds received by a microphone, and transmit an interfering signal to the microphone. Instruction sets could also cause a device to render an interface that allows a user to control noise reduction (e.g., by choosing among different environmental profiles, by operating a graphical interface having virtually movable designators, etc.). It is contemplated that a user could select two or more profiles to be used concurrently.

The flowcharts and diagrams in the Figures illustrate the architecture, functionality, and operation of possible implementations of systems, methods, and computer applications according to various embodiments of the present inventive subject matter. In this regard, each block in a flowchart could represent may represent a module, segment, or portion of code, which comprises one or more executable instructions for implementing a specified logical instruction or instructions. It should be noted that in some alternative embodiments the functions noted in a block may occur out of the order indicated in the Figure. For example, two blocks shown in succession may, in fact, be executed in the reverse order, depending on the functionality involved.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An automated noise reduction system operable by a user, comprising;

a headset comprising a speaker and a microphone; and, an audio player configured to play an audio file and implement a noise canceling application; and the application configured to render a user interface through which the user at least one of sequentially and concurrently chooses from a first pre-generated noise reduction profile and a second pre-generated noise reduction profile different from the first profile, wherein the first pre-generated noise reduction profile provides a first set of relative degrees of noise cancellation that is applied to a first set of frequency ranges, and wherein the second pre-generated noise reduction profile provides a second set of relative degrees of noise cancellation that is applied to a second set of frequency ranges based at least in part on altering amplitudes of signals sent to the speaker.

2. The automated noise cancelling system of claim 1, wherein the interface is further configured to allow the user to generate a user-generated noise reduction profile.

3. The automated noise cancelling system of claim 2, wherein the interface is configured to allow the user to generate the user-generated noise reduction profile by operating a graphical interface having virtually movable designators for different frequency ranges.

4. The automated noise cancelling system of claim 1, wherein the first pre-generated profile is an office-related profile.

5. The automated noise cancelling system of claim 1, wherein the first pre-generated profile is a home-related profile.

6. The automated noise cancelling system of claim 1, wherein the first frequency range is the second frequency range.

7. The automated noise cancelling system of claim 1, wherein the first frequent range is discontinuous from the second frequency range.

8. The automated noise cancelling system of claim 1, wherein the audio player comprises a cell phone.

9. The automated noise cancelling system of claim 1, wherein the audio player comprises a tablet computer.

10. An application operable in cooperation with (a) an audio player operated by a user, and (b) a headset comprising a speaker and a microphone, comprising;

a first instruction set operable on the audio player that causes the audio player to receive a first signal indicative of a sound received by the microphone, and to transmit to the microphone a second signal that interferes with the first signal, thereby achieving a noise reduction as perceived by the user;

a second instruction set that causes the audio player to render a user interface through which the user at least one of sequentially and concurrently selects from a first pre-generated noise reduction profile and a second pre-generated noise reduction profile different from the first profile, wherein the first pre-generated noise reduction profile provides a first set of relative degrees of noise cancellation that is applied to a first set of frequency ranges, and wherein the second pre-generated noise reduction profile provides a second set of relative degrees of noise cancellation that is applied to a second set of frequency ranges based at least in part on altering amplitudes of signals sent to the speaker.

11. The application of claim 10, further comprising a third instruction set that allows the user to generate a user-generated noise reduction profile.

12. The application of claim 11, wherein the interface is configured to allow the user to generate the user-generated noise reduction profile by operating a graphical interface having virtually movable designators for different frequency ranges.

13. The application of claim 10, wherein at least one of the first and second noise reduction profiles is an office-related profile and at least one of the first and second noise reduction profiles is a home-related profile.

14. The automated noise cancelling system of claim 10, wherein the interface allows the user to select for concurrent use the first profile and the second profile.

15. An automated noise reduction system operable by a user, comprising;

a headset comprising a speaker and a microphone; and, an audio player configured to play an audio file and implement a noise canceling application; and the application configured to render a user interface through which the user at least one of sequentially and concurrently chooses from a first pre-generated noise reduction profile and a second pre-generated noise reduction profile different from the first profile, wherein the first pre-generated noise reduction profile provides a first set of relative degrees of noise cancellation that is applied to a first set of frequency ranges, and wherein the second pre-generated noise reduction profile provides a second set of relative degrees of noise cancellation that is applied to a second set of frequency ranges based at least in part on altering phases of signals being sent to the speaker.

* * * * *